US010901053B2

(12) United States Patent
Eryaman et al.

(10) Patent No.: US 10,901,053 B2
(45) Date of Patent: Jan. 26, 2021

(54) METHODS FOR MEASURING INDUCED CURRENTS ON ELECTRICAL LEADS AND ELECTRODES IN MAGNETIC RESONANCE IMAGING

(71) Applicant: REGENTS OF THE UNIVERSITY OF MINNESOTA, Minneapolis, MN (US)

(72) Inventors: Yigitcan Eryaman, Minneapolis, MN (US); Gregor Adriany, Minneapolis, MN (US); Noam Harel, Minneapolis, MN (US); Gregory F. Molnar, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/364,382

(22) Filed: Mar. 26, 2019

(65) Prior Publication Data

US 2019/0293737 A1    Sep. 26, 2019

Related U.S. Application Data

(60) Provisional application No. 62/648,027, filed on Mar. 26, 2018.

(51) Int. Cl.
*G01V 3/00* (2006.01)
*G01R 33/28* (2006.01)
*G01R 33/483* (2006.01)
*A61B 5/055* (2006.01)
*G01R 19/00* (2006.01)

(52) U.S. Cl.
CPC ............ *G01R 33/288* (2013.01); *A61B 5/055* (2013.01); *G01R 19/0092* (2013.01); *G01R 33/285* (2013.01); *G01R 33/4835* (2013.01)

(58) Field of Classification Search
CPC .............. G01R 33/543; G01R 33/5659; G01R 33/3415; G01R 33/36; A61B 5/055
USPC ......................................................... 324/309
See application file for complete search history.

(56) References Cited

U.S. PATENT DOCUMENTS 8,319,496 B2    11/2012    Eryaman
9,268,003 B2     2/2016    Griffin
(Continued)

OTHER PUBLICATIONS

Acikel, V. et al. "Modeling of radio-frequency induced currents on lead wires during MR imaging using a modified transmission line method." Medical Physics 38.12 (2011): 6623-6632.

(Continued)

*Primary Examiner* — Walter L Lindsay, Jr.
*Assistant Examiner* — Frederick Wenderoth
(74) *Attorney, Agent, or Firm* — Quarles & Brady LLP

(57) ABSTRACT

Systems and method for measuring and mitigating radio frequency ("RF") induced currents on electrical leads, electrodes, and other electrically conductive objects present in the bore of a magnetic resonance imaging ("MRI") scanner when the MRI scanner is operated to image an object or subject are described. The methods described in the present disclosure can be implemented as a pre-scan procedure to obtain images from which the current induced on the electrical lead can be estimated. This information can then be used to adjust the RF excitation used in a subsequent pulse sequence to mitigate induced currents and reduce heating in the lead. As such, the methods described in the present disclosure provide for improved patient safety.

24 Claims, 4 Drawing Sheets

(56) References Cited

U.S. PATENT DOCUMENTS

2010/0160997 A1 6/2010 Johnson
2010/0253338 A1 10/2010 Eryaman

OTHER PUBLICATIONS

Butson, C.R., et al, 2011. Probabilistic analysis of activation volumes generated during deep brain stimulation. Neuroimage 54, 2096-2104.

Cabot, E, et al. "Evaluation of the RF heating of a generic deep brain stimulator exposed in 1.5 T magnetic resonance scanners." Bioelectromagnetics 34.2 (2013): 104-113.

Erhardt, J., et al. Should patients with brain implants undergo MRI? J. Neural. Eng. Published May 15, 2018. https://doi.org/10.1088/1741-2552/aab4e4.

Eryaman, Y., et al. 2011. Reduction of implant RF heating through modification of transmit coil electric field. Magn. Reson. Med. 65, 1305-1313.

Eryaman, Y., et al. 2013. Reduction of the radiofrequency heating of metallic devices using a dual-drive birdcage coil. Magn. Reson. Med. 69, 845-852.

Eryaman, Y., et al., 2015. Parallel transmit pulse design for patients with deep brain stimulation implants. Magn. Reson. Med. 73, 1896-1903.

Etezadi-Amoli, M., et al. 2015. Controlling radiofrequency-induced currents in guidewires using parallel transmit. Magn. Reson. Med. 74, 1790-1802.

Feng, S., et al. "A technique to evaluate MRI-induced electric fields at the ends of practical implanted lead." IEEE Transactions on Microwave Theory and Techniques 63.1 (2014): 305-313.

Golestanirad, L., et al., 2017. Construction and modeling of a reconfigurable MRI coil for lowering SAR in patients with deep brain stimulation implants. Neuroimage 147, 577-588.

Golestanirad, L., et al., 2017. Feasibility of using linearly polarized rotating birdcage transmitters and close-fitting receive arrays in MRI to reduce SAR in the vicinity of deep brain simulation implants. Magn. Reson. Med. 77, 17011712.

Griffin, G. H., et al. (2015), Safely assessing radiofrequency heating potential of conductive devices using image-based current measurements. Magn. Reson. Med., 73: 427-441.

Griswold, M.A., et al., 2002. Generalized autocalibrating partially parallel acquisitions (GRAPPA). Magn. Reson. Med. 47, 1202-1210.

Gudino, N., et al., 2015. Parallel transmit excitation at 1.5 T based on the minimization of a driving function for device heating. Med. Phys. 42, 359-371.

Hebb, A.O., et al., 2010. Semi-automatic stereotactic coordinate identification algorithm for routine localization of Deep Brain Stimulation electrodes. J. Neurosci. Methods 187, 114-119.

Henderson JM, et al. Permanent neurological deficit related to magnetic resonance imagingin a patient with mplanted deep brain stimulation electrodes for Parkinson's disease: case report. Neurosurgery 2005;57:E1063.

Husch, A., et al. 2018. PaCER—a fully automated method for electrode trajectory and contact reconstruction in deep brain stimulation. Neuroimage-Clin 17, 80-89. Available online Oct. 6, 2017.

McElcheran, C.E, et al. 2015. Investigation of parallel radiofrequency transmission for the reduction of heating in long conductive leads in 3 Tesla magnetic resonance imaging. PloS One 10. e0134379.

Min, H.K., et al., 2012. Deep brain stimulation induces Bold activation in motor and nonmotor networks: an fMRI comparison study of STN and EN/GPi DBS in large animals. Neuroimage 63, 1408-1420.

Nordbeck, P, et al. "Measuring RF-induced currents inside implants: impact of device configuration on MRI safety of cardiac pacemaker leads." Magnetic Resonance in Medicine. 61.3 (2009): 570-578.

Schirra, C.O., et al., Toward true 3D visualization of active catheters using compressed sensing. Magn Reson Med, 2009. 62(2): pp. 341-347.

Van Den Bosch, M.R., et al. 2010. New method to monitor RF safety in MRI-guided interventions based on RF induced image artefacts. Med. Phys. 37, 814-821.

Yeung, C.J., et al. 2002. RF safety of wires in interventional MRI: using a safety index. Magn. Reson. Med. 47, 187-193.

Younce, J.R., et al. 2014. Deep brain stimulation with simultaneous FMRI in rodents. J Vis Exp. e51271.

Rx Channel #1   Rx Channel #2   Rx Channel #n

METHODS FOR MEASURING INDUCED CURRENTS ON ELECTRICAL LEADS AND ELECTRODES IN MAGNETIC RESONANCE IMAGING

CROSS-REFERENCE TO RELATED APPLICATIONS

This application claims the benefit of U.S. Provisional Patent Application Ser. No. 62/648,027, filed on Mar. 26, 2018, and entitled "METHODS FOR MEASURING INDUCED CURRENTS ON ELECTRICAL LEADS AND ELECTRODES IN MAGNETIC RESONANCE IMAGING," which is herein incorporated by reference in its entirety.

STATEMENT REGARDING FEDERALLY SPONSORED RESEARCH

This invention was made with government support under EB021173 and EB015894 awarded by National Institutes of Health. The government has certain rights in the invention.

BACKGROUND

Magnetic resonance imaging ("MRI") scans induce RF currents on elongated metallic leads. These induced currents may critically increase the temperature at the lead tip. In the last decade, a number of studies were published investigating the feasibility of optimizing the transmit coils and/or the RF excitation to mitigate lead heating.

DBS leads have complex geometries involving electrically conductive wires, insulators and electrode arrays. Although previous methods have demonstrated induced current detection and heating prediction, these methods were demonstrated for only simple conductor geometries. However, for most DBS leads it is not possible to measure the induced current close to the electrodes due to image artifacts resulting from the complex geometry of wire to electrode connections at the tip. This problem is more constraining for DBS lead designs that include multiple electrodes. Yet, the maximum heating occurs at the electrodes; therefore, the current needs to be measured on the conductor close to the electrode to predict the heating accurately. But, such measurements are practically difficult to achieve because the magnetic field distribution at the vicinity of the electrode is distorted by the electrode geometry. Therefore, the simplified view of magnetic field being generated due to a single current element flowing on a wire is not valid around the electrodes.

SUMMARY OF THE DISCLOSURE

The present disclosure addresses the aforementioned drawbacks by providing a method for measuring radio frequency ("RF") current induced in an electrically conductive object positioned in a bore of a magnetic resonance imaging ("MRI") scanner. The method includes acquiring first data from a first slice in a subject. The first slice is proximal to an electrically conductive object and contains an electrically conductive wire connected to the electrically conductive object. Second data are acquired from a second slice in the subject. The second slice is distal to the electrically conductive object. A first image is reconstructed from the first data, and a second image is reconstructed from the second data. The first image is processed with a computer system to compute a location of a center of the electrically conductive wire and a location of a transmit null point. An angular position of the transmit null point is computed with the computer system based on the location of the center of the electrically conductive wire and the location of the transmit null point. The second image is processed with the computer system to estimate a transmit RF field incident on the electrically conductive object. A magnitude of an induced current in the electrically conductive wire and a phase of the induced current in the electrically conductive wire are then computed with the computer system using the angular position of the transmit null point and the estimation of the transmit RF field incident on the electrically conductive object.

It is another aspect of the present disclosure to provide a method for generating an implant friendly ("IF") radio frequency ("RF") excitation with an MRI system. The method includes acquiring with the MRI system, pre-scan data from a volume containing an electrically conductive object having connected thereto an electrically conductive wire. The pre-scan data include first data acquired from a first slice containing the electrically conductive wire and second data acquired from a second slice that does not contain the electrically conductive wire. Currents that were induced in at least one of the electrically conductive object or the electrically conductive wire while the pre-scan data were acquired are calculated from the pre-scan data. A channel weight for each channel in a multi-channel transmitter is calculated based on the calculated induced currents. Collectively, the channel weights define an IF RF excitation. An IF RF excitation is then generated in the volume with the MRI system and the multi-channel transmitter using the calculated channel weights. Generating the IF RF excitation does not significantly increase a temperature in either the electrically conductive object or the electrically conductive wire The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and method for measuring and mitigating radio frequency ("RF") induced currents on electrical leads, electrodes, and other electrically conductive objects present in the bore of a magnetic resonance imaging ("MRI") scanner when the MRI scanner is operated to image an object or subject. The methods described in the present disclosure can be implemented as a pre-scan procedure to obtain images from which the current induced on the electrical lead can be estimated. This information can then be used to adjust the RF excitation used in a subsequent pulse sequence to mitigate induced currents and reduce heating in the lead. As such, the methods described in the present disclosure provide for improved patient safety and improved image quality when imaging in the presence of electrical leads, electrodes, and other electrically conductive objects.

Figure 1:
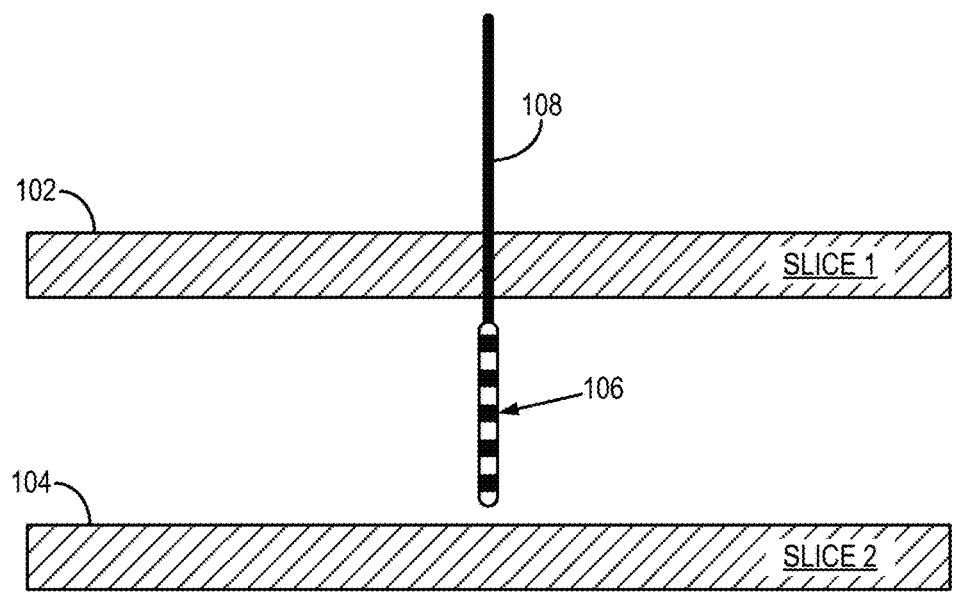
FIG. 1 is a representation of an electrode, such as a deep brain stimulation ("DBS") electrode and a first slice that is proximal to the electrode and a second slice that is distal to the electrode, and where the first slice also contains a conductive lead connected to the electrode.

As shown in FIG. 1, the method generally includes acquiring images from a first slice 102 and a second slice 104 that are both spatially adjacent an electrode 106. The first slice 102 is proximal to the electrode 106 and is positioned to contain the conductive lead 108 extending from the electrode. In addition, the first slice 102 is preferably positioned such that it does not include the electrode 106. The second slice 104 is distal to the electrode 106 and is positioned to preferably not include the electrode 106. The first slice 102 and the second slice 104 can be oriented in any suitable orientation. In some implementations, the first slice 102 and the second slice 104 can both be axial slices. In other implementations the first slice 102, the second slice 104, or both, can be coronal slices, sagittal slices, or oblique slices.

As will be described in more detail below, an image is obtained from the first slice in a manner that the location of the lead and the location of a transmit null point can be determined. An image obtained from the second slice is used to estimate the transmit magnetic field (i.e., $B_1^+$). These quantities can be used to estimate a measurement of the current induced in the lead. By measuring the induced current in the lead, RF pulses can be designed to mitigate the induced current, which can reduce heating in the lead. For instance, the magnitude and phase of the induced current can be used to compute an implant friendly ("IF") excitation, which can be used in a variety of different pulse sequences to acquire data from the subject with reduced heating in the lead. The measurement of the induced current can also be used to analyze different heating conditions that result from different amounts of induced current.

Additionally or alternatively, the measurement of the induced current can be used to calculate specific absorption rate ("SAR") at the electrode (e.g., at the electrode tip) based on a linear relationship between the induced current and the square root of the SAR observed at the electrode. In a similar manner, the temperature at the electrode (e.g., at the electrode tip) can be estimated from the induced current. This information about SAR is useful because it allows for the induced current to be measured once and used, for example, in long RF heating studies of new electrode, or other medical device, designs. If the slope of the linear relationship between induced current and square root of SAR is known, the induced current can be measured and used to predict how much an electrode or other medical device will heat up based on the slope of the line. Thus, rather than spending hours to measure temperature for different lead trajectories, these measurements could be reliably estimated based on quickly obtained current measurements.

As mentioned, images obtained from the slices adjacent an electrode can be used to estimate the induced current in an electrical lead connected to that electrode. The signal intensity of a magnetic resonance image obtained from the $m^{th}$ receiver coil in a multi-channel receiver array can be described as, $$SI_m \approx \left(B_{1,m}^- - (j\cos\phi + \sin\phi) \cdot \frac{\mu_0 I_m^r}{4\pi r}\right) \cdot \left(B_1^+ + (j\cos\phi - \sin\phi) \cdot \frac{\mu_0 I^t}{4\pi r}\right); \quad (1)$$

where $B_{1,m}^-$ is the receiver sensitivity of the $m^{th}$ individual receiver coil observed at the vicinity of the lead; $I_m^r$ is the current that would be induced on the lead due to reciprocity when the $m^{th}$ receiver coil was used as transmit coil and excited with a unit current; $\phi$ and $r$ denote the cylindrical coordinates centered on the lead at a given plane of interest; $B_1^+$ denotes the transmit sensitivity of the body coil; and $I^t$ denotes the current induced on the lead due to excitation of the body coil.

Figure 2:
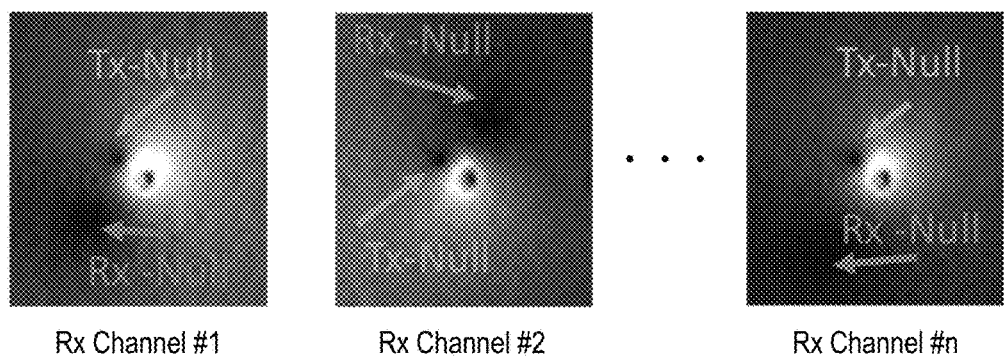
FIG. 2 depicts a series of images reconstructed from data acquired on different receive channels from a first slice.

Eqn. (1) assumes a small flip-angle approximation. When Eqn. (1) is set to zero, two solutions can exist. Therefore, for each image acquired from an individual receiver element, it is expected that two null locations for the signal intensity will exist. These two null locations occur due to interaction of the lead with the receive and the transmit elements, separately. FIG. 2 shows a series of images depicting the two null points around a conductive lead. Note that the location of the receiver null is different for each receiver element. But, the location of the transmit null is fixed among receivers. The location of the transmit null depends on the current flowing on the lead and the transmit field excited by the body coil. Thus, information about the transmit null can be used to estimate the induced current on the lead.

Using a sum-of-squares reconstruction, the magnitude of the resulting image will have signal intensity observed around the lead as follows:

$$SI \approx \left|B_1^+ + (j\cos\phi - \sin\phi) \cdot \frac{\mu_0 I^t}{4\pi r}\right| \cdot \sqrt{\sum_m \left|B_{1,m}^- - (j\cos\phi + \sin\phi) \cdot \frac{\mu_0 I_m^r}{4\pi r}\right|^2}. \quad (2)$$

Figure 3:
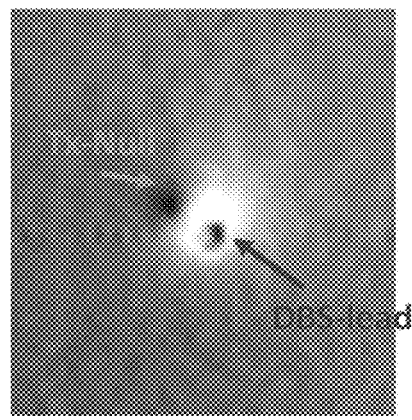
FIG. 3 depicts a sum-of-squares combination of the images shown in FIG. 2.

Eqn. (2) has a single null (i.e., SI=0). Because the receive coils are geometrically distributed, and each receive element contributes to a different receive-null location, the square-sum expression is a non-zero function. Assuming that the signal contribution of all channels is comparable, a relatively uniform receive profile can be produced as a result of this reconstruction. Therefore, the magnitude square-sum images have a single null whose location is determined only by the transmit field of the coil, $B_1^+$, and by the current induced on the lead by the transmit coil, $I^t$. An example of such a sum-of-squares image is shown in FIG. 3. It is a discovery of the present disclosure that this relationship exists, and that it can be relied upon to use multi-channel receiver coils and parallel acquisition to measure the RF induced current, $I^t$.

Although the exact value of $B_1^+$ may not be measurable from a single image of the artifact around the lead, it can be approximated by the $B_1^+$ measured adjacent the electrode (e.g., underneath the electrode in a plane that does not contain the conductive lead or electrode) where the contribution of the RF induced current, $I^t$, is approximately zero.

Assuming that the nominal flip angle prescribed by the scanner, $\alpha_{nom}$, at the adjacent plane is accurate, the $B_1^+$ field can be estimated as, $$B_1^+ = \frac{\alpha_{nom}}{\gamma \int_0^{TR} p(t)dt} \quad (3)$$

where p(t) denotes the RF pulse waveform and TR is the repetition time of the pulse sequence. Once an estimated value of $B_1^+$ has been found, then the magnitude and the phase of the induced current, $I^t$, can be calculated from the null location $(r_0, \phi_0)$ as follows:

$$|I^t| = \frac{|B_1^+| 4\pi r_0}{\mu_0}; \quad (4)$$

$$\angle I^t = \phi_0. \quad (5)$$

The measurements described above can be performed using quadrature excitation. After those measurements have been made, similar measurements can be repeated with an arbitrary excitation pattern. In those instances, the transmit field, $B_1^+$, can be calculated by scaling the quadrature transmit field, $B_{1,quad}^+$, with the following scaling factor, $$\kappa = \frac{\overline{S}}{\overline{S}_{quad}}; \quad (6)$$

where $\overline{S}_{quad}$ and $\overline{S}$ are the mean image intensities measured in the adjacent plane (e.g., underneath the electrode) observed due to quadrature and arbitrary excitation patterns, respectively.

Figure 4:
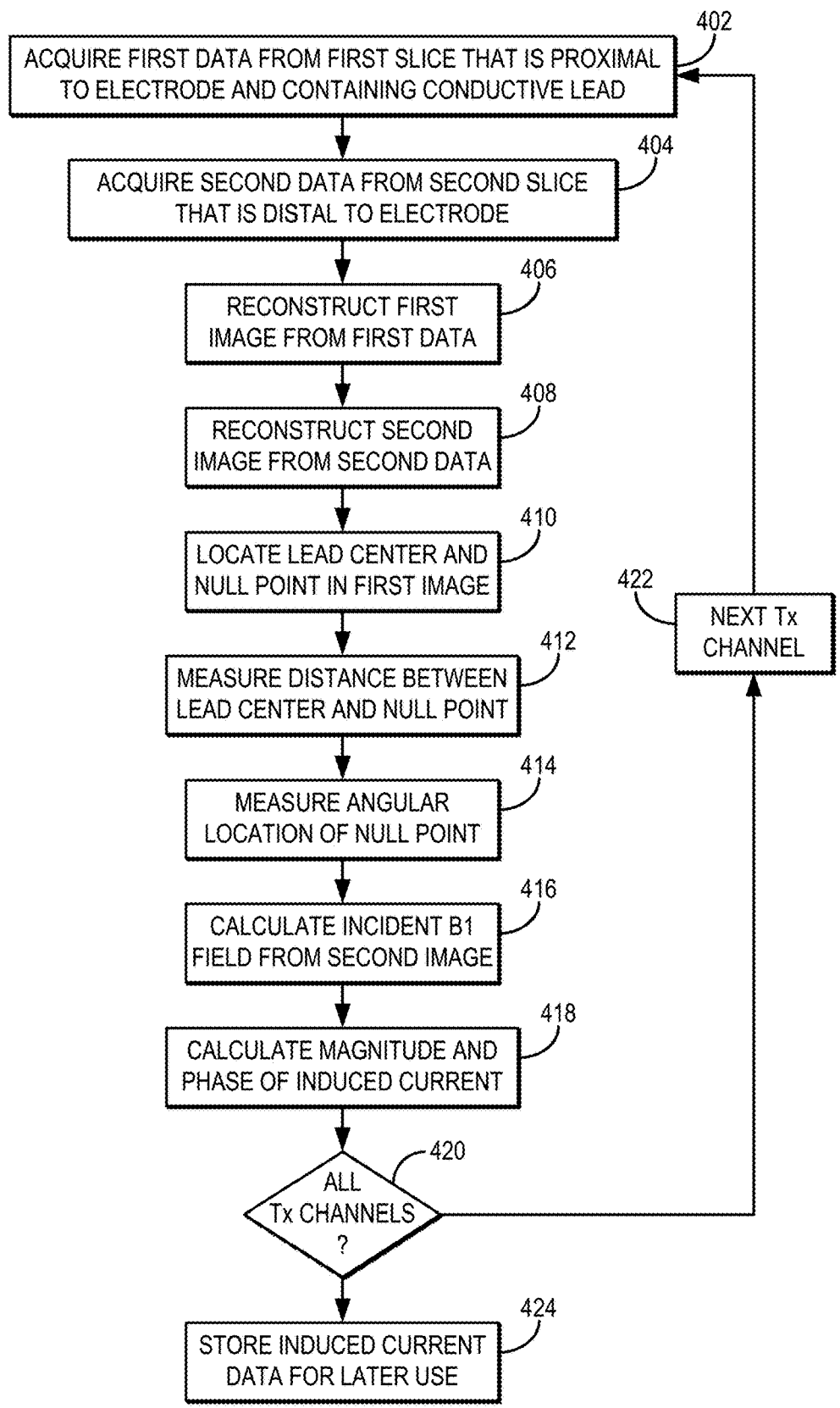
FIG. 4 is a flowchart that sets forth the steps of an example method for measuring induced currents in a conductive lead or other metallic implant or object using a magnetic resonance imaging ("MRI") system.

Referring now to FIG. 4, a flowchart is illustrated as setting forth the steps of an example method for measuring induced currents in a conductive lead using an MRI system. The method includes acquiring first data from a first slice in a subject that is proximal to an electrode (or other electrically conductive object) and that contains a conductive lead (or other electrically conductive wire) connected thereto, as indicated at step 402. Preferably, the location of the first slice is selected to be close to, but not containing, the electrode. In some implementations the first data can also include data acquired from a plurality of different slices, each proximal to the electrode. Preferably, each of such images would contain the conductive lead. In these embodiments, the plurality of first slices can all be parallel, or some or all of the plurality of first slices can have different orientations. As one example, first data can be acquired from a plurality of parallel first slices. In some implementations, such data can be acquired using a simultaneous multislice acquisition. As another example, first data can be acquired from slices oriented in different planes. For instance, first data can be acquired from one slice oriented in the axial plane, and another slice oriented in the sagittal plane, the coronal plane, or an oblique plane. In this manner, the induced current on the lead can be measured in these other planes. Second data are also acquired from a second slice in the subject that is distal to the electrode, as indicated at step 404. Preferably, the location of the second slice is selected to be close to, but not contain, the electrode.

In some embodiments, the locations of the first and second slices can be selected or otherwise determined from a pre-scan of the subject. As one example, the pre-scan can include a localizer scan. In addition, the laser alignment provided by the MRI scanner can be used to further assist in positioning the subject in the bore of the MRI scanner such that the first and second slices can be positioned as described in the present disclosure. Unlike previous approaches, the pre-scan method described in the present disclosure does not require on B1+ mapping sequences or complex matching between modeled and measured B1− variations around metallic wires or objects.

Preferably, the first data and the second data are acquired using a pulse sequence that implements low power, low flip angle RF pulses. The RF pulses can be generated using quadrature excitation. In some embodiments, the pulse sequence is a gradient echo ("GRE") pulse sequence. The first data and the second data can be acquired sequentially, or in some instances can be acquired simultaneously.

Depending on the transmit and receive hardware of the MRI scanner used to acquire the first and second data, the first and second data can be acquired using a single channel receiver or a multi-channel receiver. Similarly, the RF excitation used in the pulse sequence can be generated using a single channel transmitter or a multi-channel transmitter.

In some embodiments, the first data, second data, or both, can be acquired using parallel imaging or other suitable accelerated imaging techniques. For instance, in-plane acceleration can be used when acquiring the first data, second data, or both. In these instances, a GRAPPA-based or SENSE-based reconstruction can then be used. In other implementations, a simultaneous multislice acquisition may be used to provide acceleration along the slice-encoding direction.

A first image is reconstructed from the first data, as indicated at step 406. When the first data are acquired using a multi-channel receiver the first image can be reconstructed based on a sum-of-squares combination of the images reconstructed on each receiver channel. It will be appreciated, too, that other reconstruction techniques can be readily used to reconstruct the first image from the first data. Based on the location of the first slice, this first image will depict the conductive lead connected to the electrode, but preferably not the electrode itself. As noted above, this first image will also depict a transmit null point, the location and angular position of which can be used to estimate the induced current in the lead.

A second image is reconstructed from the second data, as indicated at step 408. When the second data are acquired using a multi-channel receiver the second image can be reconstructed based on a sum-of-squares combination of the images reconstructed on each receiver channel. It will be appreciated, too, that other reconstruction techniques can be readily used to reconstruct the second image from the second data. Based on the location of the second slice, this second image will not depict the electrode. As noted above, the second image can be processed to estimate the transmit RF field incident on the electrode, which can be used to estimate the induced current in the lead.

The first image is analyzed to determine a spatial location of the conductive lead (i.e., the lead center) and the spatial location of a null point (e.g., a transmit null point), as indicated at step 410. For instance, the spatial location of the lead center and the null point can be determined as locations in the image matrix corresponding to the first image. The distance between the lead center and the null point is then computed and stored for later use, as indicated at step 412. The first image is then analyzed to compute the angular location of the null point, as indicated at step 414. The angular location of the null point can be determined by using the location of the lead center as the origin of a coordinate system and measuring the angular location of the null point within that coordinate system. The coordinate system may be a cylindrical coordinate system, but in other embodiments could also be another coordinate system, such as a spherical coordinate system. As an example, the angular position of the null point can be computed using a coordinate system transformation to transform the location of the null point in the image matrix (e.g., a Cartesian coordinate) to a cylindrical coordinate $(r_0,\phi_0)$ position using the location of the lead center as the origin of that coordinate system.

The second image is then analyzed to compute an electrode-free magnetic field, which corresponds to the incident magnetic field of the transmit coil, as indicated at step 416. This incident magnetic field can be computed based on Eqn. (3) above. The magnitude and phase of the induced current on the conductive lead is then computed, as indicated at step 418. The phase may be a relative phase. The magnitude and phase of the induced current can be computed based on Eqns. (4) and (5) above, based on the angular position of the null point, $(r_0,\phi_0)$, and the transmit RF field incident on the electrode, $B_1^+$.

A determination is then made at decision block 420 whether the induced current has been measured for each transmit channel. If not, then the next transmit channel is selected, as indicated at step 422, and used to provide RF excitation when acquiring another set of first and second data. Steps 402-418 are thus repeated to measure the induced current associated with the new transmit channel. In some implementations, the excitation pattern used in these subsequent repetitions can be varied.

When the induced current has been measured for each transmit channel, as determined at decision block 420, then the induced current measurements are stored as induced current data for later use, as indicated at step 424.

In some instances, the conductive lead may be oriented at an oblique angle relative to the main magnetic field of the MRI system. When this is the case, Eqns. (1), (2), (4), and (5) can be modified to account for this different geometric arrangement. To account for the oblique orientation when estimating the induced current in the conductive lead, the orientation of the conductive lead relative to the main magnetic field can be determined and used to compute the location of the transmit null. As one example, the orientation of the conductive lead can be determined from images obtained with a localizer scan, which may also be used to prescribe the location and orientation of the imaging slices, as described above. These localizer (or "scout") images can be used to calculate the orientation of the conductive lead with respect to the axis of the main magnetic field.

As one example, the induced current data can be used to design RF pulses for use in subsequent imaging of the subject, such that the induced current in the lead is mitigated. For instance, the magnitude and phase of the induced current can be used to compute an implant friendly ("IF") excitation, which can be used in a variety of different pulse sequences to acquire data from the subject with reduced heating in the lead. As an example, the IF excitation can be used in turbo spin echo ("TSE"), 2D ultra short echo time ("UTE"), echo planar imaging ("EPI"), fluid attenuated inversion recovery ("FLAIR"), steady state free precession ("SSFP"), and other such pulse sequences, such as those that may be used for diffusion weighted imaging, perfusion weighted imaging, and so on. As another example, the induced current data can be used to analyze heating at different conditions, and to estimate predictions of SAR in different lead configurations, as described above.

Figure 5:
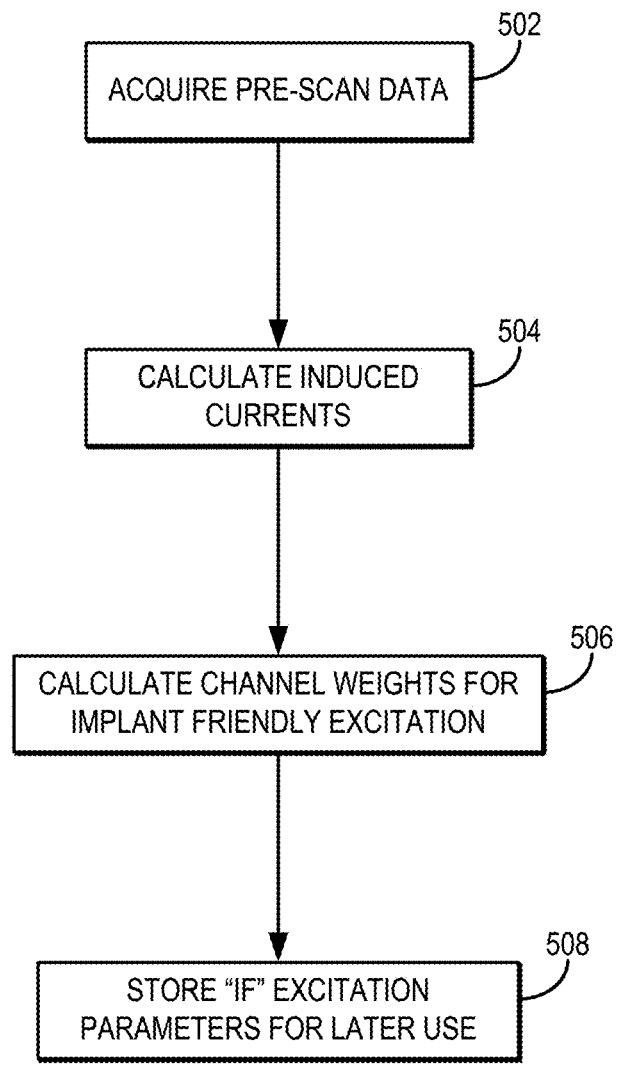
FIG. 5 is an example workflow for determining an implant friendly excitation based on measuring induced currents using the methods described in the present disclosure.

Referring now to FIG. 5, a flowchart is illustrated as setting forth the steps for an example workflow in which an IF excitation is determined and confirmed. The method includes acquiring pre-scan data, as indicated at step 502. The pre-scan data may be acquired as described above. For example, the pre-scan data may include first data acquired from a first imaging plane and second data acquired from a second imaging place, as described above. In some instances, the pre-scan data are acquired by performing the same pulse sequence a plurality of time, each time with a different excitation pattern. As one non-limiting example, when using a multi-channel transmitter the different excitation patterns may include a quadrature excitation, excitation using only one of the channels, or excitation using a combination of different channels. When using multiple channels to generate excitation, the different channels can be driven in-phase, out-of-phase, or combinations thereof. Induced currents are then calculated from the pre-scan data, as indicated at step 504. For instance, the induced currents can be calculated as described above.

The IF excitation is computed next using the induced currents, as indicated at step 506. Computing the IF excitation may include calculating channel weights that satisfy the following:

$$\sum_{n=1}^{N} \alpha_n I_n = 0; \qquad (7)$$

$$\sum_{n=1}^{N} \alpha_n^2 = 1; \qquad (8)$$

where $I_n$ is the current induced using the nth excitation pattern for n=1, ..., N different excitation patterns used for acquiring the pre-scan data. As a non-limiting example, the number of different excitation patterns may correspond to at least the number of channels in a multi-channel transmitter. For instance, in a two-channel transmitter, a first excitation pattern may include transmitting with only the first channel (e.g., "Ch1") and a second excitation pattern may include transmitting with only the second channel (e.g., "Ch2"). In this instance, the current induced from the first excitation, $I_1$, and the current induced from the second excitation, $I_2$, can be calculated and used to compute the channel weights for the IF friendly excitation. In order to measure $I_1$ and $I_2$, separate scans using Ch1, Ch2, and quadrature mode excitations are used. A scan with quadrature mode provides signal calibration data for Ch1 and Ch2 and also additional data regarding the unmitigated induced current as a comparison.

The computed IF excitation, which may include the channel weights to apply to transmit channels in order to deliver IF friendly excitation, is then stored for later use, as indicated at step 508. Storing the IF friendly excitation may include, for instance, storing the channel weights. The stored IF excitation can then be communicated or otherwise used to operate the transmitter to deliver the IF friendly excitation to a subject in which an electrode or other metallic implant or object is located.

Figure 6:
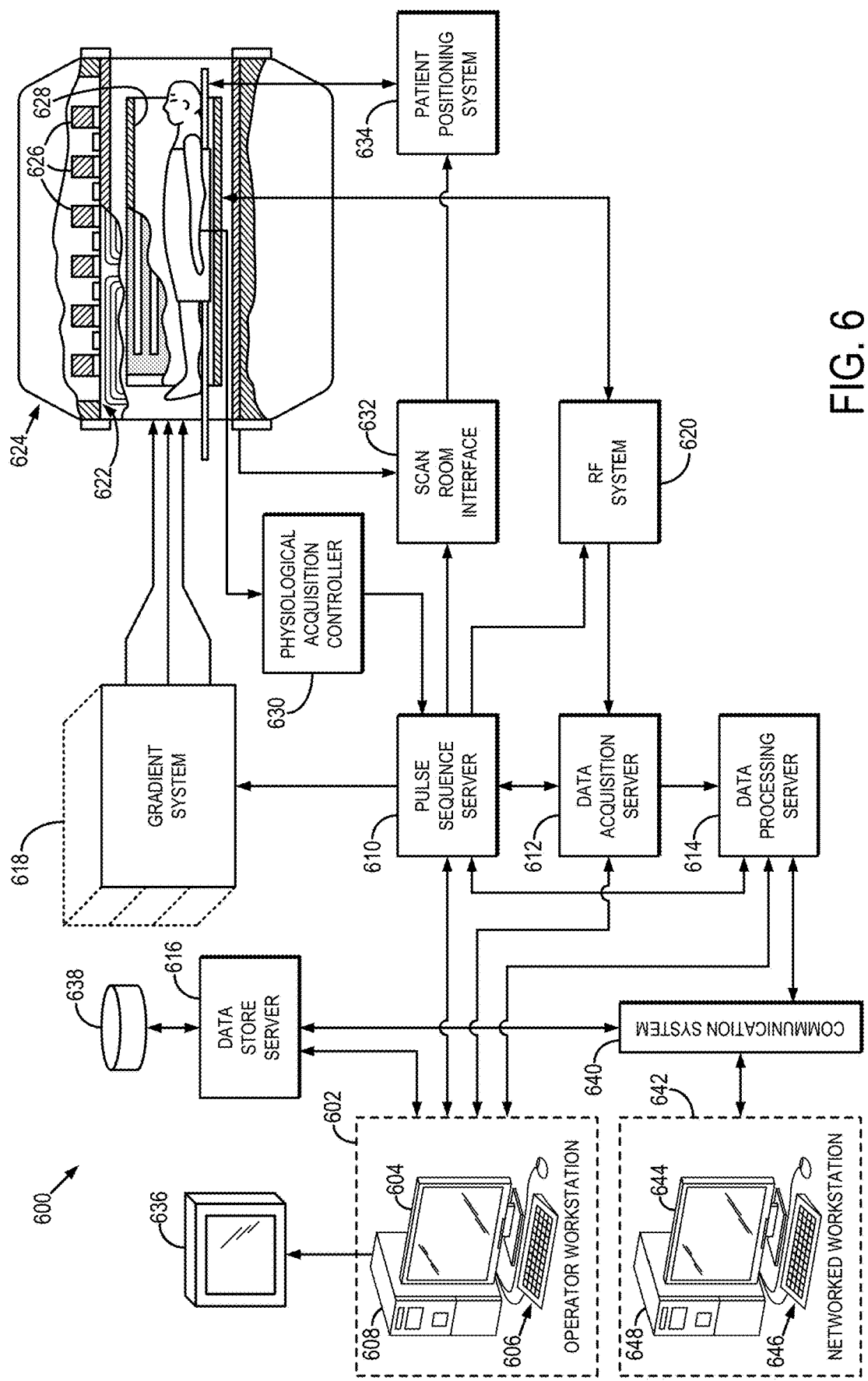
FIG. 6 is a block diagram of an example MRI system that can implement the methods described in the present disclosure.

Referring particularly now to FIG. 6, an example of an MRI system 600 that can implement the methods described here is illustrated. The MRI system 600 includes an operator workstation 602 that may include a display 604, one or more input devices 606 (e.g., a keyboard, a mouse), and a processor 608. The processor 608 may include a commercially available programmable machine running a commercially available operating system. The operator workstation 602 provides an operator interface that facilitates entering scan parameters into the MRI system 600. The operator workstation 602 may be coupled to different servers, including, for example, a pulse sequence server 610, a data acquisition server 612, a data processing server 614, and a data store server 616. The operator workstation 602 and the servers 610, 612, 614, and 616 may be connected via a communication system 640, which may include wired or wireless network connections.

The pulse sequence server 610 functions in response to instructions provided by the operator workstation 602 to operate a gradient system 618 and a radiofrequency ("RF") system 620. Gradient waveforms for performing a prescribed scan are produced and applied to the gradient system 618, which then excites gradient coils in an assembly 622 to produce the magnetic field gradients $G_x$, $G_y$, and $G_z$ that are used for spatially encoding magnetic resonance signals. The gradient coil assembly 622 forms part of a magnet assembly 624 that includes a polarizing magnet 626 and a whole-body RF coil 628.

RF waveforms are applied by the RF system 620 to the RF coil 628, or a separate local coil to perform the prescribed magnetic resonance pulse sequence. Responsive magnetic resonance signals detected by the RF coil 628, or a separate local coil, are received by the RF system 620. The responsive magnetic resonance signals may be amplified, demodulated, filtered, and digitized under direction of commands produced by the pulse sequence server 610. The RF system 620 includes an RF transmitter for producing a wide variety of RF pulses used in MRI pulse sequences. The RF transmitter is responsive to the prescribed scan and direction from the pulse sequence server 610 to produce RF pulses of the desired frequency, phase, and pulse amplitude waveform. The generated RF pulses may be applied to the whole-body RF coil 628 or to one or more local coils or coil arrays.

The RF system 620 also includes one or more RF receiver channels. An RF receiver channel includes an RF preamplifier that amplifies the magnetic resonance signal received by the coil 628 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (9);$$

and the phase of the received magnetic resonance signal may also be determined according to the following relationship:

$$\varphi = \tan^{-1}\left(\frac{Q}{I}\right). \qquad (10)$$

The pulse sequence server 610 may receive patient data from a physiological acquisition controller 630. By way of example, the physiological acquisition controller 630 may receive signals from a number of different sensors connected to the patient, including electrocardiograph ("ECG") signals from electrodes, or respiratory signals from a respiratory bellows or other respiratory monitoring devices. These signals may be used by the pulse sequence server 610 to synchronize, or "gate," the performance of the scan with the subject's heart beat or respiration.

The pulse sequence server 610 may also connect to a scan room interface circuit 632 that receives signals from various sensors associated with the condition of the patient and the magnet system. Through the scan room interface circuit 632, a patient positioning system 634 can receive commands to move the patient to desired positions during the scan.

The digitized magnetic resonance signal samples produced by the RF system 620 are received by the data acquisition server 612. The data acquisition server 612 operates in response to instructions downloaded from the operator workstation 602 to receive the real-time magnetic resonance data and provide buffer storage, so that data is not lost by data overrun. In some scans, the data acquisition server 612 passes the acquired magnetic resonance data to the data processor server 614. In scans that require information derived from acquired magnetic resonance data to control the further performance of the scan, the data acquisition server 612 may be programmed to produce such information and convey it to the pulse sequence server 610. For example, during pre-scans, magnetic resonance data may be acquired and used to calibrate the pulse sequence performed by the pulse sequence server 610. As another example, navigator signals may be acquired and used to adjust the operating parameters of the RF system 620 or the gradient system 618, or to control the view order in which k-space is sampled. In still another example, the data acquisition server 612 may also process magnetic resonance signals used to detect the arrival of a contrast agent in a magnetic resonance angiography ("MRA") scan. For example, the data acquisition server 612 may acquire magnetic resonance data and processes it in real-time to produce information that is used to control the scan.

The data processing server 614 receives magnetic resonance data from the data acquisition server 612 and processes the magnetic resonance data in accordance with instructions provided by the operator workstation 602. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 614 are conveyed back to the operator workstation 602 for storage. Real-time images may be stored in a data base memory cache, from which they may be output to operator display 602 or a display 636. Batch mode images or selected real time images may be stored in a host database on disc storage 638. When such images have been reconstructed and transferred to storage, the data processing server 614 may notify the data store server 616 on the operator workstation 602. The operator workstation 602 may be used by an operator to archive the images, produce films, or send the images via a network to other facilities.

The MRI system 600 may also include one or more networked workstations 642. For example, a networked workstation 642 may include a display 644, one or more input devices 646 (e.g., a keyboard, a mouse), and a processor 648. The networked workstation 642 may be located within the same facility as the operator workstation 602, or in a different facility, such as a different healthcare institution or clinic.

The networked workstation 642 may gain remote access to the data processing server 614 or data store server 616 via the communication system 640. Accordingly, multiple networked workstations 642 may have access to the data processing server 614 and the data store server 616. In this manner, magnetic resonance data, reconstructed images, or other data may be exchanged between the data processing server 614 or the data store server 616 and the networked workstations 642, such that the data or images may be remotely processed by a networked workstation 642.

The present disclosure has described one or more preferred embodiments, and it should be appreciated that many equivalents, alternatives, variations, and modifications, aside from those expressly stated, are possible and within the scope of the invention.

The invention claimed is:

1. A method for measuring radio frequency (RF) current induced in an electrically conductive object positioned in a bore of a magnetic resonance imaging (MRI) scanner, the steps of the method comprising:
   (a) acquiring with an MRI system, first data from a first slice in a subject, the first slice being proximal to an electrically conductive object having attached thereto an electrically conductive wire, wherein the first slice contains the electrically conductive wire;
   (b) acquiring with the MRI system, second data from a second slice in the subject, the second slice being distal to the electrically conductive object;
   (c) reconstructing a first image from the first data;
   (d) reconstructing a second image from the second data;
   (e) processing the first image with a computer system to compute a location of a center of the electrically conductive wire and a location of a transmit null point;
   (f) computing with the computer system, an angular position of the transmit null point based on the location of the center of the electrically conductive wire and the location of the transmit null point;
   (g) processing the second image with the computer system to compute an estimation of a transmit radio frequency (RF) field incident on the electrically conductive object; and
   (h) computing with the computer system a magnitude of an induced current in the electrically conductive wire and a phase of the induced current in the electrically conductive wire using the angular position of the transmit null point and the estimation of the transmit RF field incident on the electrically conductive object.

2. The method as recited in claim 1, wherein the first data and the second data are acquired following a quadrature RF excitation.

3. The method as recited in claim 2, further comprising computing with the computer system a scaling factor for scaling the transmit RF field based on an arbitrary RF excitation, wherein the scaling factor is computed based on a ratio of a signal intensity in the second image and a signal intensity in an image obtained using the arbitrary RF excitation.

4. The method as recited in claim 1, wherein both the first slice and the second slice are axial slices.

5. The method as recited in claim 1, wherein the first data and the second data are acquired using a multi-channel receiver, and wherein the first image and the second image are each reconstructed using a reconstruction algorithm that implements a sum-of-squares.

6. The method as recited in claim 1, wherein steps (a)-(h) are repeated for each channel in a multi-channel transmitter in order to determine an induced current for each channel in the multi-channel transmitter.

7. The method as recited in claim 6, further comprising determining a channel weight for each channel in the multi-channel transmitter, wherein the channel weights define an implant friendly (IF) excitation pattern that when transmitted using the multi-channel transmitter does not significantly increase a temperature in at least one of the electrically conductive object or the electrically conductive wire.

8. The method as recited in claim 7, wherein the channel weights, $\alpha_n$, are determined based on $$\sum_{n=1}^{N} \alpha_n I_n = 0 \text{ and } \sum_{n=1}^{N} \alpha_n^2 = 1,$$

wherein $I_n$ is the induced current for the $n^{th}$ channel of the multi-channel transmitter, and N is a number of channels in the multi-channel transmitter.

9. The method as recited in claim 8, further comprising generating an IF excitation with the multi-channel transmitter using the determined channel weights.

10. The method as recited in claim 1, wherein the first data are acquired from a plurality of first slices in the subject, each of the plurality of first slices being proximal to the electrically conductive object and containing at least a portion of the electrically conductive wire.

11. The method as recited in claim 10, wherein the plurality of first slices are all oriented parallel to a same plane.

12. The method as recited in claim 11, wherein the first data are acquired using a simultaneous multislice acquisition to simultaneously acquire data from the plurality of first slices.

13. The method as recited in claim 10, wherein at least some of the plurality of first slices are oriented in different planes.

14. The method as recited in claim 1, wherein the electrically conductive object comprises an electrode and the electrically conductive wire comprises a conductive lead connected to the electrode.

15. The method as recited in claim 1, further comprising estimating specific absorption rate (SAR) from the magnitude of the induced current in the electrically conductive wire and the phase of the induced current in the electrically conductive wire.

16. The method as recited in claim 1, further comprising estimating a temperature from the magnitude of the induced current in the electrically conductive wire and the phase of the induced current in the electrically conductive wire.

17. A method for generating an implant friendly (IF) radio frequency (RF) excitation with a magnetic resonance imaging (MRI) system, the steps of the method comprising:
   (a) acquiring with an MRI system, pre-scan data from a volume containing an electrically conductive object having connected thereto an electrically conductive wire, wherein the pre-scan data comprise first data acquired from a first slice containing the electrically conductive wire and second data acquired from a second slice that does not contain the electrically conductive wire;

(b) calculating from the pre-scan data, induced currents that were induced in at least one of the electrically conductive object or the electrically conductive wire while the pre-scan data were acquired;

(c) calculating a channel weight for each channel in a multi-channel transmitter based on the calculated induced currents, wherein the channel weights define an IF RF excitation; and (d) generating in the volume, an IF RF excitation with the MRI system and the multi-channel transmitter using the calculated channel weights, wherein generating the IF RF excitation does not significantly increase a temperature in either the electrically conductive object or the electrically conductive wire.

18. The method as recited in claim 17, wherein the first data and the second data are acquired following a quadrature RF excitation.

19. The method as recited in claim 17, wherein the pre-scan data are acquired using a plurality of different RF excitation patterns such that different first data and second data are acquired for each RF excitation pattern.

20. The method as recited in claim 19, wherein calculating the induced currents includes calculating a different induced current for each of the plurality of different RF excitation patterns.

21. The method as recited in claim 20, wherein the channels weights are determined based on $$\sum_{n=1}^{N} \alpha_n I_n = 0 \text{ and } \sum_{n=1}^{N} \alpha_n^2 = 1,$$

wherein $I_n$ is the induced current for the $n^{th}$ channel of the multi-channel transmitter, and N is a number of channels in the multi-channel transmitter.

22. The method as recited in claim 17, wherein the electrically conductive object comprises an electrode and the electrically conductive wire comprises a conductive lead connected to the electrode.

23. The method as recited in claim 17, further comprising estimating specific absorption rate (SAR) from the calculated induced currents.

24. The method as recited in claim 17, further comprising estimating a temperature from the calculated induced currents.

* * * * *